United States Patent
Hasselbach et al.

(10) Patent No.: US 7,655,072 B2
(45) Date of Patent: Feb. 2, 2010

(54) PROCESS FOR PURIFYING $CO_2$ GAS STREAMS

(75) Inventors: Hans-Joachim Hasselbach, Gelnhausen (DE); Jose Vanrobaeys, Kalmthout (BE); Martin Körfer, Kalmthout-Heide (BE)

(73) Assignee: Degussa AG, Dusseldorf (DE)

( * ) Notice: Subject to any disclaimer, the term of this patent is extended or adjusted under 35 U.S.C. 154(b) by 638 days.

(21) Appl. No.: 11/185,367

(22) Filed: Jul. 20, 2005

(65) Prior Publication Data

US 2006/0016334 A1 Jan. 26, 2006

(30) Foreign Application Priority Data

Jul. 22, 2004 (DE) .................. 10 2004 035 465

(51) Int. Cl.
*B01D 53/14* (2006.01)
(52) U.S. Cl. .................. 95/235; 95/237; 423/243.01; 423/242.2; 562/559; 562/575; 562/556
(58) Field of Classification Search .................. 95/204, 95/213, 235, 237; 423/243.01, 242.2; 96/290; 261/114.2, 114.5; 562/559, 575, 556
See application file for complete search history.

(56) References Cited

U.S. PATENT DOCUMENTS

| 2,557,920 | A | * | 6/1951 | White ........................ 548/499 |
| 3,636,098 | A | * | 1/1972 | Takesaburo shima et al. ............... 562/559 |
| 3,668,221 | A | * | 6/1972 | Shima et al. ............. 548/499 |
| 3,878,057 | A | | 4/1975 | Mannsfeld |
| 4,048,232 | A | | 9/1977 | Koberstein et al. |
| 4,069,251 | A | * | 1/1978 | Mannsfeld et al. ........ 562/559 |
| 4,303,621 | A | * | 12/1981 | Lussling et al. ........... 423/189 |
| 4,319,044 | A | * | 3/1982 | Matsumoto et al. ....... 562/559 |
| 5,770,769 | A | | 6/1998 | Geiger et al. |
| 5,990,349 | A | | 11/1999 | Geiger et al. |
| 7,172,179 | B2 | * | 2/2007 | Jacobs et al. ................. 261/97 |

FOREIGN PATENT DOCUMENTS

| DE | EP-0839804 A2 | * | 5/1998 |
| EP | 0 780 370 A2 | | 6/1997 |
| EP | 0 839 804 A2 | | 5/1998 |
| JP | EP-839804 A2 | * | 5/1998 |

* cited by examiner

*Primary Examiner*—Duane Smith
*Assistant Examiner*—Ives Wu
(74) *Attorney, Agent, or Firm*—Smith, Gambrell & Russell, LLP

(57) ABSTRACT

A process for purifying $CO_2$ offgas streams to free them of chemical compounds, and to the recycling of the purified gas streams into the production process.

30 Claims, 2 Drawing Sheets

PROCESS FOR PURIFYING $CO_2$ GAS STREAMS

The invention relates to a process for purifying $CO_2$ offgas streams to free them of chemical compounds and to the recycling of the purified gas streams into the production process.

Such offgases occur in particular in the preparation of methionine and comprise, in addition to methyl mercaptan, generally also ammonia, hydrocyanic acid and steam.

Such a methionine process is described, for example, in EP-B 0780370=U.S. Pat. Nos. 5,770,769 and 5,990,349.

The underlying process steps can be illustrated as follows:

Step 1: formation of 5-(2-methylmercapto)hydantoin

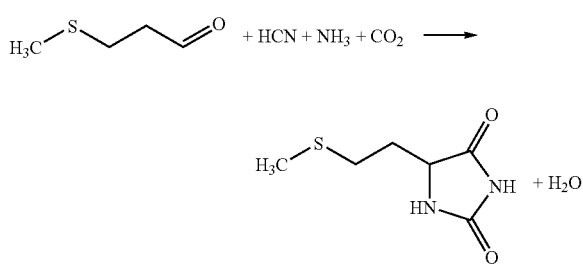

Step 2: hydrolysis of the hydantoin to form the methionine potassium salt

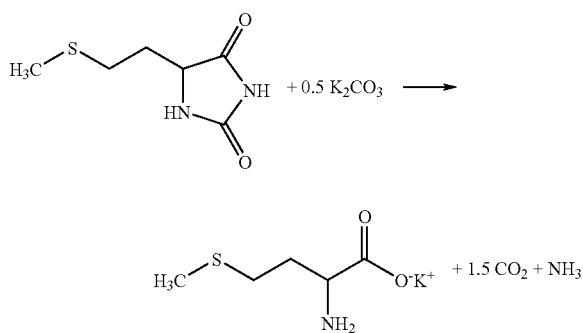

Step 3: stripping of $NH_3$ and $CO_2$ from the hydrolysis mixture

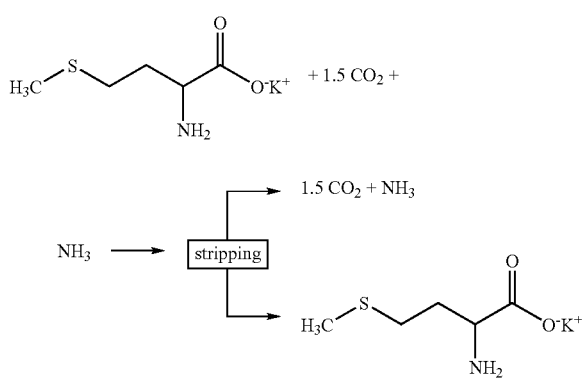

Step 4: release of solid methionine from its potassium salt

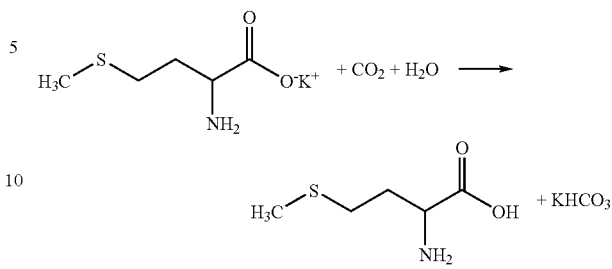

Step 5: separation of solid methionine and mother liquor

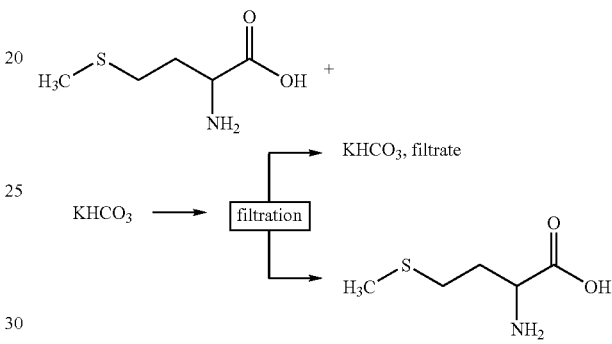

Step 6: heat treatment of the mother liquor to release $CO_2$ and recycling into step 2:

$$KHCO3 \to 0.5\ K_2CO_3 + 0.5\ CO_2$$

The overall equation of the methionine synthesis by the above process has the following appearance:

$$MMP + HCN + H_2O \to \text{methionine}$$

The recycling of $K_2CO3$ and $NH_3$ according to the above-mentioned partial steps does not constitute any problem.

However, when steps 2 and 3 are considered, it can be seen that, from a stoichiometric point of view, 1.5 mol of $CO_2$ can be released from these per mole of $NH_3$. According to EP 0 780 370 A, these volatile components may be recycled into the stage of hydantoin formation (step 1).

However, according to the stoichiometry of the reaction, 0.5 mol of $CO_2$ leaves this stage without reaction unutilized as offgas.

Simple recycling is not possible since the chemical analysis of the offgas shows that it comprises, based on the $CO_2$ content, methyl mercaptan (Mc) in amounts of 1-10% by weight. The methyl mercaptan-containing offgas cannot be utilized in the methionine precipitation (step 4), since the product which has been filtered off would be greatly odour-afflicted. In addition, the methyl mercaptan, owing to its acid character, would accumulate as potassium methylmercaptide in the process solutions, which would lead to disruptions in the methionine workup. The methyl mercaptan content of the offgas from the hydantoin synthesis has two causes. One is that the methylmercaptopropionaldehyde (MMP) used as a raw material, as a result of the process, always comprises a certain methyl mercaptan residue content (see U.S. Pat. Nos. 4,048,232 and 3,878,057); the other is that methyl mercaptan can form by thermal decomposition of methionine, mainly in the hydantoin hydrolysis supported by potassium carbonate (step 2). The thermal decomposition of methionine is also described in EP 839 804.

For the reasons mentioned, the offgas is incinerated according to the prior art, in the course of which $CO_2$ and methyl mercaptan are lost and considerable costs for the combustion simultaneously arise.

U.S. Pat. No. 4,319,044 already discloses a process for preparing 5-(2-methylmercapto)hydantoin, in which the hydrogen cyanide present in the offgas consisting mainly of $CO_2$ and the methyl mercaptan are recovered by multistage scrubbing. According to this process, the offgas is initially contacted either with an ammonium carbonate or a dilute hydantoin solution in order to bind HCN. The HCN-laden solution is recycled into the hydantoin synthesis. In a second scrubbing stage, the offgas which still comprises methyl mercaptan and ammonia is scrubbed with water in order to remove $NH_3$. In the third scrubbing stage, the offgas is counter-scrubbed with methylmercaptopropionaldehyde (MMP), which binds the methyl mercaptan as hemithioacetal. A disadvantage of this process is that $CO_2$, as the quantitatively most significant proportion of the offgas stream, escapes unutilized. Moreover, an additional waste stream is formed in the process mentioned as a result of the emission of the water scrubbing described there, which comprises the toxic substances ammonia and methyl mercaptan, whose disposal is associated with high costs.

The process described in the U.S. Pat. No. 4,319,044 additionally possesses the disadvantage that the offgas stream, in the course of the scrubbing process, comes into contact with MMP last.

Hence, it is saturated with MMP at least in accordance with the specific vapour pressure and is only recyclable to a limited extent.

SUMMARY OF THE INVENTION

It is an object of the invention to purify offgas streams consisting mainly of $CO_2$ to free them of chemical compounds contained therein in such a way that the purified $CO_2$ can subsequently be recycled into the production process.

The invention provides a process for purifying $CO_2$-containing gas streams having a content of methyl mercaptan, in which the gas is scrubbed in the specified sequence
a) with water or with water in which methylmercaptopropionaldehyde (MMP) is present dissolved up to a maximum of the solubility limit,
b) subsequently with MMP and
c) then with water, and
d) the thus purified $CO_2$ is recycled into the production process.

DETAILED DESCRIPTION OF THE INVENTION

The process is particularly suitable when the gas comprises one or more additional fractions selected from the group of hydrocyanic acid, ammonia and water.

Preference is given to a process for purifying $CO_2$ offgases obtained in a process for preparing methionine, in which 3-methylmercaptopropionaldehyde (MMP), hydrogen cyanide, ammonia and carbon dioxide, or those components from which the aforementioned components can be prepared, are converted to 5-(2-methylmercaptoethyl)hydantoin, this is hydrolysed and the methionine is precipitated with the introduction of $CO_2$, where the $CO_2$-containing offgas exiting from the hydantoin synthesis reactor is subjected to the abovementioned at least three-stage scrubbing process, and
a) the resulting scrubbing liquids are recycled into the preparation process for methionine or its precursors, and
b) the purified $CO_2$ gas stream is introduced into an alkali metal salt solution of the methionine-containing reactor, and methionine is precipitated from this salt.

The offgas exiting from the hydantoin synthesis reactor contains generally 60 to 75% by weight of $CO_2$, 0.01 to 0.1% by weight of hydrocyanic acid, 1 to 10% by weight of methyl mercaptan, 0.5 to 5% by weight of ammonia and 15 to 25% by weight of water.

The ammonia-containing scrubbing liquid from washing step a) is introduced into the hydantoin synthesis reactor.

The methyl mercaptan-containing scrubbing liquid from scrubbing step b) is introduced into the MMP synthesis, and the MMP-containing scrubbing liquid from scrubbing step c) is used as scrubbing liquid for scrubbing step a).

In scrubbing step b), the amount of MMP used is selected in such a way that the molar ratio of MMP:methyl mercaptan (gaseous) is 1:1 to 3:1, in particular 1:1 to 2:1.

The scrubbing is carried out at a temperature of 10 to 60° C., in particular 10 to 40° C.

The pressure in the scrubbing apparatus is generally 1 to 10 bar higher than that in the precipitation reactor for methionine. Suitable scrubbing apparatuses are in particular multistage columns having intermediate column bottoms or columns having valve or bubble-cap trays.

Figure 2:
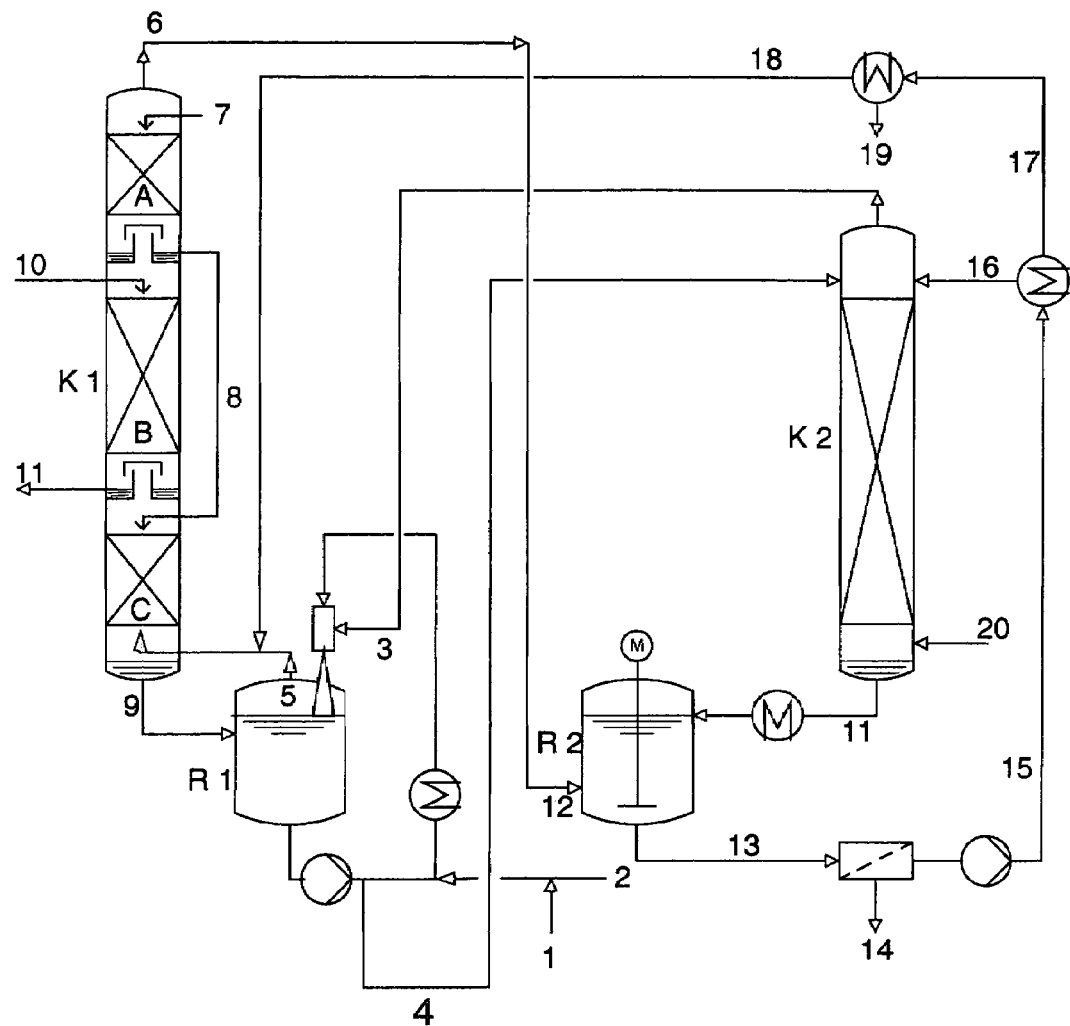
FIG. 2 shows a schematic flow chart according to another embodiment of the invention.

The scrubbing is effected in countercurrent. The purified gas has a $CO_2$ content of >98% by weight, in particular >99% by weight to 99.8% by weight. In addition, the $CO_2$-containing gas obtained from the workup of the mother liquor obtained in the methionine process (step 6), from which the water has been condensed out, can be passed through the scrubbing apparatus (FIG. 2).

5-(2-Methylmercaptoethyl)hydantoin is prepared according to EP 0 780 370 A by preparing a solution of hydrogen cyanide in 3-methylmercaptopropionaldehyde and a solution of ammonia and carbon dioxide in water, rapidly and intimately mixing these solutions and reacting them. The solution of hydrogen cyanide in 3-methylmercaptopropionaldehyde is appropriately adjusted in such a way that it consists of equimolar proportions of hydrogen cyanide and 3-methylmercaptopropionaldehyde, or else comprises excess proportions of hydrogen cyanide. In general, it is advantageous not to select the proportion of hydrogen cyanide in the solution at greater than 1.1 mol per mole of 3-methylmercaptopropionaldehyde; the solution preferably contains 1.005 to 1.05 mol of hydrogen cyanide per mole of 3-methylmercaptopropionaldehyde.

The solution of ammonia and carbon dioxide in water may be a saturated or dilute solution; advantageously, the content of ammonia is not below about 5% by weight. The molar ratio of ammonia to carbon dioxide is appropriately about 1.2 to 4.0 mol, preferably 1.6 to 1.8 mol, of ammonia per mole of carbon dioxide. The solution of hydrogen cyanide in 3-methylmercaptopropionaldehyde is mixed with the solution of ammonia and carbon dioxide in water in such a way that a molar ratio of ammonia to 3-methylmercaptopropionaldehyde of about 1.2 to 6:1.0 is appropriately present in the mixture, preferably 2.0 to 4.0:1.0, in particular 2.5 to 3.0:1.0. The reaction is performed at ambient temperature or higher, appropriately at temperatures above 60° C., advantageously between about 80° C. and 140° C. Preference is given to selecting temperatures between 80 and 130° C., in particular between 90 and 120° C. Although the reaction can proceed at any pressure, it is appropriate to work at elevated pressure; advantageous pressures are found to be up to 20 bar, in particular pressures which are 2 to 3 bar above the equilibrium pressure of the reaction mixture. The reaction time depends upon the reaction conditions, in particular upon the temperature and upon the quantitative ratios.

In the preferred procedure, it is particularly advantageous to introduce the solution of hydrogen cyanide in 3-methylmercaptopropionaldehyde and the solution of ammonia and carbon dioxide in water into a reaction mixture of these substances, i.e. into a mixture formed beforehand in the reaction of the solutions, in which the reaction of hydantoin has proceeded to completion or in part, and to perform the reaction in this mixture.

It is particularly advantageous to select a continuous procedure, to conduct the reaction mixture in circulation for this purpose, to constantly feed the solutions of hydrogen cyanide in 3-methylmercaptopropionaldehyde and of ammonia and carbon dioxide in water at two adjacent points in this circuit, and to constantly remove a corresponding proportion of the reaction mixture from the circulation at another point.

The process for preparing methionine or an alkali metal salt of methionine by hydrolysis of 5-(2-methylmercaptoethyl)hydantoin in the presence of an aqueous solution comprising alkali metal and carbon dioxide, and optional further reaction to give methionine, the hydrolysis being carried out at least at the start in the presence of at least 0.1 eq., in particular up to 7 eq., of ammonia per equivalent of 5-(2-methylmercaptoethyl)hydantoin, is likewise known from the EP document.

It has been found that it is particularly advantageous when the hydrolysis is carried out from the start in the presence of alkali metal and carbon dioxide, i.e. that in particular a mixture of alkali metal compounds is present, in particular alkali metal hydrogencarbonate, alkali metal carbonate, alkali metal hydroxide, alkali metal being in particular potassium and sodium. The amount of alkali metal and carbon dioxide is appropriately at least the stoichiometric amount based on the hydantoin. This can be distinctly exceeded at the upper end. A molar ratio with an excess of about 3:1 based on the hydantoin is particularly advantageous; in principle, it can be assumed that an even greater excess is even more favourable. However, particular preference is given in practice to ratios of about 1.5:1-2:1. According to the invention, some ammonia is additionally added, which is correspondingly likewise partly also present in the form of ammonia compounds. It is particularly advantageous in this context when, at the start of the hydrolysis, max. 7 mol of ammonia (incl. ammonium compounds) are present per mole of 5-(2-methylmercaptoethyl)hydantoin. This achieves progress of the hydrolysis virtually without by-product formation and in good yields, and secondly only little alkali metal carbonate, if any, precipitates out. It is particularly advantageous in this context when ammonia and/or carbon dioxide, if appropriate together with water, are discharged from the reaction system during the hydrolysis. This allows the reaction conditions to be controlled particularly favourably, so that still no alkali metal carbonate precipitates out and the reaction proceeds to completion.

The hydrolysis processes are favourably carried out at a temperature of 120 to 250° C. and correspondingly a pressure of 5 to 30 bar. In this range, very good conversions and low by-product formation result. It is also advantageous when the alkali metal component is used in an at least equimolar amount based on the 5-(2-methylmercaptoethyl)hydantoin. In that case, in addition to the full hydrolysis, the corresponding alkali metal salt of methionine is also obtained virtually quantitatively. The hydrolysis solution preferably also already comprises methionine or its salt at the start; this too has a favourable, presumably autocatalytic effect on the hydrolysis.

In this procedure, virtually all of the ammonia and all of the carbon dioxide can advantageously be removed from the hydrolysis solution in the course of or after the hydrolysis, so that the hydrolysate can be removed substantially free of ammonia and carbon dioxide.

Here too, it is particularly advantageous to carry out the process continuously. It is very particularly advantageous in this context that the processes described hitherto can be connected together, in particular as a fully continuous process in which carbon dioxide and ammonia can be recycled.

Methionine is released from alkali metal methionate in aqueous solution by introducing carbon dioxide, the release preferably being carried out in a stirred cell reactor with intensive mixing or in a stirred reactor with virtually ideal mixing.

In the release of the methionine from the aqueous solution by means of carbon dioxide, it is particularly advantageous when the carbon dioxide is introduced into the aqueous solution via a nozzle device in the region of the bottom. This in turn promotes the release of the methionine. Moreover, the release is advantageously carried out at a pressure of 1 to 30 bar, preferably also at a temperature of 0 to 100° C.

Very particularly advantageously, an aqueous solution is used which is substantially free of ammonia.

The last procedure too is particularly favourably carried out continuously.

The inventive method makes it possible to operate the methionine process without $CO_2$ loss. Further undesired off-gas or wastewater streams do not occur.

EXAMPLES

Example 1

As described in EP 0780370, the hydantoin hydrolysis (K 2) is carried out preferably at a pressure of 7-9 bar and the release of the methionine from its potassium salt with $CO_2$ in (R 2) at a pressure of 2 to 5 bar. It is therefore particularly advantageous to keep the plant parts hydantoin hydrolysis (K 2), hydantoin reactor (R 1) and the $CO_2$ scrubbing system together at a higher pressure than the reactor (R 2), so that the purified $CO_2$ (6) passes into the precipitation reactor (R 2) without further conveying units. It is further advantageous to combine the 3-stage $CO_2$ scrubbing as explained above in one column having two intermediate column bottoms in order to minimize the apparatus demands.

Figure 1:
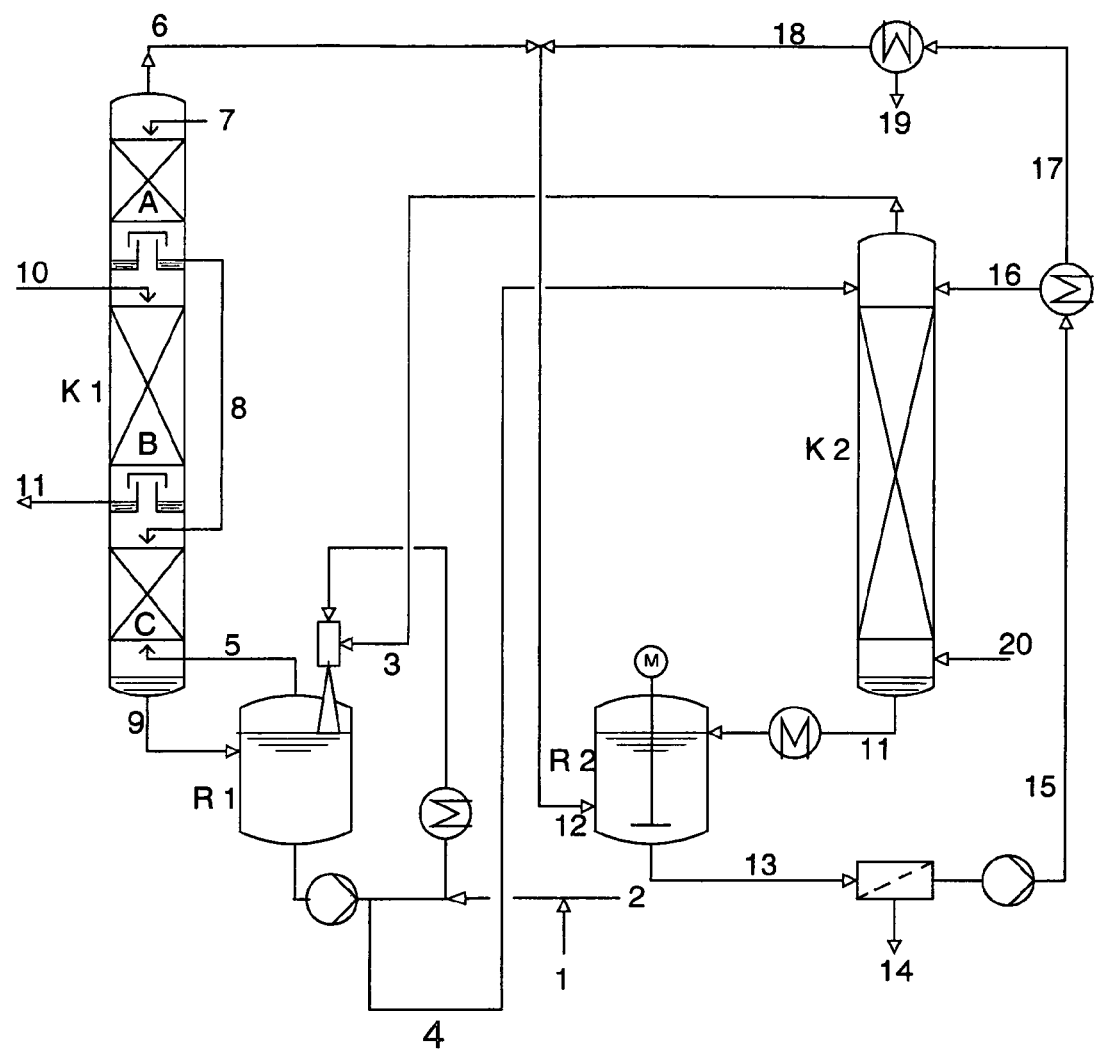
FIG. 1 shows a schematic flow chart according to the invention.

With reference to FIG. 1 and the process steps detailed at the outset, the invention is illustrated in detail:

HCN (1) and MMP (2) are fed to the continuously operated hydantoin reactor (R 1) (step 1). Via 3, the reaction partners $NH_3$ and $CO_2$ also pass into it from the hydrolysis and stripping column (K 2) (step 2+3). Excess Mc- and $NH_3$-containing $CO_2$ leaves the hydantoin reactor (R 1) via 5 and is washed to free it of $NH_3$ with aqueous solution 8 in the lower section of the scrubbing column (K 1, C). Subsequently, the gas enters the scrubbing zone (K 1, B) from below and is washed to free it of Mc in countercurrent with MMP (10). Finally, the gas is finely purified with water (7) and leaves the column (K 1) via 6. The Mc-laden MMP (hemithioacetal) leaves the column (K 1) via 11 and is fed to MMP synthesis.

The purified $CO_2$ is combined with the $CO_2$ obtained from the workup (18) and serves to precipitate the methionine from the hydrolysis solution (11) in the reactor (R 2) (step 4). The suspension (13) is filtered, the filtercake (14) sent to further workup (step 5). The filtrates (15) are concentrated by evaporation (step 6). The concentrate (16) serves as the $K_2CO_3$ source for the hydantoin hydrolysis in the column (K 2). The energy supply and the stripping effect are brought about by the steam supply 20 (step 2+3).

From the vapours of the evaporative concentration, water (19) is condensed out and the $CO_2$ which remains thereafter (18) is combined with the $CO_2$ from the scrubbing column (K 1) and fed to the reactor R 2 (step 4).

The reactive absorption of Mc into MMP can be carried out particularly advantageously when the column portion (K 1, B) consists of valve or bubble-cap trays or a comparable construction. This technical design has the advantage that it enables a minimal MMP to Mc gas ratio. This minimizes the cost and inconvenience of conveying the amount of MMP used for the scrubbing. In the present case, it is advantageously possible to quantitatively scrub out the Mc content in the $CO_2$ gas with a minimal, i.e. almost stoichiometric, amount of MMP.

This process does not comprise any additionally unutilized offgas/wastewater streams.

It is also possible to pass the $CO_2$-containing offgas stream formed in the workup of the mother liquor fully or partly (step 6) likewise through the scrubber (FIG. 2).

This is advantageous in order to recover the methyl mercaptan likewise present therein. Typically, this stream contains 97 to 99% by weight of $CO_2$, 0.1 to 1% by weight of water and 0.1 to 1% by weight of methyl mercaptan.

This shifts the $CO_2$ content in the overall offgas stream to be scrubbed to higher values in comparison to the content in the offgas from the hydantoin synthesis reactor. The reduction in the concentration of the remaining constituents has no influence on the effectiveness of the scrubbing.

Example 2

A plant as described in FIG. 1 is operated with a production output of 100 kg/h of methionine.

In the hydantoin reactor R1, an offgas amount of 22.1 kg/h with the composition of 68% by weight of $CO_2$, 27% by weight of water, 3.6% by weight of methyl mercaptan, 0.9% by weight of. $NH_3$ and 0.5% by weight of other components is obtained at 80° C.

This crude gas is treated in countercurrent in the three-stage column K1, A, B, C, the operating pressure at the top of the column being 6 bar gauge.

In zone C of the column K1, the gas stream is scrubbed with 15 kg/h of water at 30° C. which is drawn from the discharge of zone A.

On entry into the scrubbing zone B of the column K1, the gas stream has the composition: 91% by weight of $CO_2$, 4.8% by weight of methyl mercaptan, 3.6% by weight of water and 0.4% by weight of other components.

In the scrubbing zone B, washing is effected in countercurrent at 20° C. with 2 kg/h of methylmercaptopropionaldehyde. Afterwards, the gas stream has the composition: 99.8% by weight of $CO_2$, 0.01% by weight of MMP and <0.2% by weight of other components. Methyl mercaptan is no longer detectable by gas chromatography.

For fine purification, the gas is also conducted through the zone A and freed of entrained MMP with 15 kg/h of water.

The thus purified gas has a content of >99.8% by weight of $CO_2$.

Further variations and modifications of the foregoing will be apparent to those skilled in the art and are intended to be encompassed by the claims appended hereto. German priority application 10 2004 035 465.0 is relied on and incorporated herein by reference.

The invention claimed is:

1. Process for preparing methionine comprising the steps of converting the following components: 3-methylmercapto-propionaldehyde (MMP), hydrogen cyanide, ammonia and carbon dioxide, or sources of those components, to 5-(2-methylmercaptoethyl)hydantoin, hydrolyzing said 5-(2-methylmercaptoethyl)hydantoin and precipitating the methionine with introduction of $CO_2$, subjecting $CO_2$-containing offgas exiting from a hydantoin synthesis reactor to a scrubbing process for purifying the $CO_2$-containing offgas stream having a content of methyl mercaptan, the scrubbing process of the gas stream comprising the specified sequence of steps:
   a) scrubbing with water or with water in which methylmercapto-propionaldehyde (MMP) is present dissolved up to a maximum of solubility limit,
   b) subsequently scrubbing with MMP,
   c) then scrubbing with water to obtain a purified $CO_2$,
   d) recycling the purified $CO_2$ gas stream is recycled into the production process,
   e) then recycling resulting scrubbing liquids into the process for preparing methionine or its precursors, and
   f) introducing the purified $CO_2$ gas stream into a reactor containing a solution of an alkali metal salt solution of methionine, and precipitating methionine from said alkali metal,
   in which scrubbing liquid from the first scrubbing step a) is passed into the hydantoin synthesis reactor.

2. Process according to claim 1 in which the scrubbing liquid from the second scrubbing step b) is passed into an MMP synthesis.

3. Process according to claim 1 in which the scrubbing liquid from the third scrubbing step c) is used as scrubbing liquid for the scrubbing step a).

4. Process for purifying a $CO_2$-containing gas stream having a content of methyl mercaptan, comprising scrubbing the gas stream in the specified sequence of steps:
   a) scrubbing with water or with water in which methylmercapto-propionaldehyde (MMP) is present dissolved up to a maximum of the solubility limit,
   b) subsequently scrubbing with MMP and
   c) then scrubbing with water to obtain a purified $CO_2$ gas, and
   d) introducing the purified $CO_2$ gas stream into an alkali metal salt solution of methionine and precipitating methionine from said alkali metal salt,
   process in which a multistage column with intermediate column bottoms is used and scrubbing is effected in countercurrent.

5. Process according to claim 4 in which a column having valve or bubble-cap trays is used.

6. Process according to claim 5 in which the $CO_2$-containing gas stream is scrubbed in scrubbing step b) with MMP, the molar MMP:methylmercaptan (gaseous) ratio being 1:1 to 2:1.

7. Process according to claim 1 in which the $CO_2$-containing gas stream is scrubbed at 10 to 60° C.

8. Process according to claim 1 in which the $CO_2$-containing gas stream is scrubbed at a pressure which is 1 to 10 bar higher than that established in a precipitation reactor for methionine.

9. Process according to claim 1 in which the $CO_2$-containing gas stream formed in the workup of the mother liquor obtained in precipitation of methionine with $CO_2$ is passed fully or partly through a scrubbing apparatus.

10. Process according to claim 1, in which a multistage column with intermediate column bottoms is used and scrubbing is effected in countercurrent.

11. Process according to claim 2, in which a multistage column with intermediate column bottoms is used and scrubbing is effected in countercurrent.

12. Process according to claim 3, in which a multistage column with intermediate column bottoms is used and scrubbing is effected in countercurrent.

13. Process according to claim 1, in which a column having valve or bubble-cap trays is used.

14. Process according to claim 1, in which the $CO_2$-containing gas stream is scrubbed in scrubbing step b) with MMP, the molar MMP:methylmercaptan (gaseous) ratio being 1:1 to 2:1.

15. Process according to claim 1, in which the $CO_2$-containing gas stream is scrubbed at 10 to 60° C.

16. Process according to claim 4, in which the $CO_2$-containing gas stream is scrubbed at a pressure which is 1 to 10 bar higher than that established in a precipitation reactor for methionine.

17. Process according to claim 6, in which the $CO_2$-containing gas stream is scrubbed at a pressure which is 1 to 10 bar higher than that established in a precipitation reactor for methionine.

18. Process according to claim 7, in which the $CO_2$-containing gas stream is scrubbed at a pressure which is 1 to 10 bar higher than that established in a precipitation reactor for methionine.

19. Process according to claim 10, in which a column having valve or bubble-cap trays is used.

20. Process according to claim 11, in which a column having valve or bubble-cap trays is used.

21. Process according to claim 12, in which a column having valve or bubble-cap trays is used.

22. Process according to claim 19, in which the $CO_2$-containing gas stream is scrubbed in scrubbing step b) with MMP, the molar MMP:methylmercaptan (gaseous) ratio being 1:1 to 2:1.

23. Process according to claim 20, in which the $CO_2$-containing gas stream is scrubbed in scrubbing step b) with MMP, the molar MMP:methylmercaptan (gaseous) ratio being 1:1 to 2:1.

24. Process according to claim 21, in which the $CO_2$-containing gas stream is scrubbed in scrubbing step b) with MMP, the molar MMP:methylmercaptan (gaseous) ratio being 1:1 to 2:1.

25. Process according to claim 22, in which the $CO_2$-containing gas stream is scrubbed at a pressure which is 1 to 10 bar higher than that established in a precipitation reactor for methionine.

26. Process according to claim 23, in which the $CO_2$-containing gas stream is scrubbed at a pressure which is 1 to 10 bar higher than that established in a precipitation reactor for methionine.

27. Process according to claim 24, in which the $CO_2$-containing gas stream is scrubbed at a pressure which is 1 to 10 bar higher than that established in a precipitation reactor for methionine.

28. Process according to claim 13, in which the $CO_2$-containing gas stream is scrubbed at a pressure which is 1 to 10 bar higher than that established in a precipitation reactor for methionine.

29. Process according to claim 14, in which the $CO_2$-containing gas stream is scrubbed at a pressure which is 1 to 10 bar higher than that established in a precipitation reactor for methionine.

30. Process according to claim 15, in which the $CO_2$-containing gas stream is scrubbed at a pressure which is 1 to 10 bar higher than that established in the precipitation reactor for methionine.

\* \* \* \* \*